United States Patent [19]

Kobayashi et al.

[11] Patent Number: 5,026,772

[45] Date of Patent: Jun. 25, 1991

[54] LYOPHILIZED PHARMACEUTICAL COMPOSITION OF NEOCARZINOSTATIN DERIVATIVE

[75] Inventors: Mitsugu Kobayashi, Yaizu; Go Ohtani, Tokyo; Jun Sekino, Yaizu; Toshimitsu Konno; Hiroshi Maeda, both of Kumamoto, all of Japan

[73] Assignee: Yamanouchi Pharmaceutical Co., Ltd., Tokyo, Japan

[21] Appl. No.: 237,950

[22] Filed: Aug. 29, 1988

[30] Foreign Application Priority Data

Sep. 1, 1987 [JP] Japan .............................. 62-218639

[51] Int. Cl.$^5$ ...................... C08G 63/48; C08G 63/91; C08L 89/00; A01N 25/00
[52] U.S. Cl. .................................... 525/54.1; 524/54; 524/56; 524/58; 514/777; 514/778
[58] Field of Search ................... 525/54.1; 524/54, 56, 524/58; 514/777, 778

[56] References Cited

U.S. PATENT DOCUMENTS

| | | |
|---|---|---|
| 3,637,640 | 1/1972 | Huber . |
| 4,182,752 | 1/1980 | Maeda et al. ................ 525/328 |
| 4,457,916 | 7/1984 | Hayashi et al. ............... 424/85.2 |
| 4,714,611 | 12/1987 | Yasaburgo et al. ............ 530/351 |
| 4,732,933 | 3/1988 | Maeda et al. ................. 525/54.1 |

FOREIGN PATENT DOCUMENTS

| | | |
|---|---|---|
| 0136791 | 4/1985 | European Pat. Off. . |
| 0260796 | 3/1988 | European Pat. Off. . |
| 2285855 | 4/1976 | France . |
| 2532178 | 3/1984 | France . |
| 27-21752 | 10/1942 | Japan . |
| 58-146504 | 9/1983 | Japan . |
| 59-25333 | 2/1984 | Japan . |
| 59-25364 | 2/1984 | Japan . |
| 59-59625 | 4/1984 | Japan . |
| 59-181224 | 10/1984 | Japan . |
| 60-59000 | 4/1985 | Japan . |
| 60-75432 | 4/1985 | Japan . |
| 60-75499 | 4/1985 | Japan . |
| 60-155136 | 8/1985 | Japan . |

OTHER PUBLICATIONS

Chemical Abstracts, vol. 85, No. 22, Nov. 29th, 1976, p. 449, abstract No. 166665a.
Chemical Abstracts, vol. 93, No. 1, Jul. 7th, 1980, p. 317, abstact No. 13083z.
Chemical Abstracts, vol. 105, No. 9, Nov. 10th, 1986, p. 371, abstract No. 178320d.
Kohno, M., et al., "Studies on the Stability of Antitumor Protein, Neocarzinostatin", *The Japanese Journal of Antibiotics*, vol. XXVII, No. 6, Dec. 1974, p. 714, (English-Language Abstract).

*Primary Examiner*—Nathan M. Nutter
*Attorney, Agent, or Firm*—Spencer & Frank

[57] ABSTRACT

A lyophilized pharmaceutical composition comprised of a neocarzinostatin derivative having the formula (SMA)-(NCS)-(SMA), is made by a method including dissolving the neocarzinostatin derivative and stabilizing agent comprising at least one saccharide selected from the group consisting of monosaccharides, disaccharides and dextran in an aqueous buffer solution having a pH ranging from about 7.5 to about 9.5, the stabilizing agent being present in an amount by weight (titer) which is at least equal to that of the neocarzinostatin derivative, to provide a solution; adjusting the pH of the solution to provide a pH-adjusted solution having a pH of about 8.0±0.5; sterilizing the pH-adjusted solution by filtration to provide a sterilized solution; and lyophilizing the sterilized solution.

16 Claims, No Drawings

LYOPHILIZED PHARMACEUTICAL COMPOSITION OF NEOCARZINOSTATIN DERIVATIVE

BACKGROUND OF THE INVENTION

1. Field of the Invention

This invention relates to a lyophilized pharmaceutial composition of a neocarzinostatin derivative (hereinafter abbreviated as SMANCS) having styrene-maleic acid copolymeric residue.

2. Related Art Statement

SMANCS is a derivative of neocarzinostatin (hereinafter abbreviated as NCS), and is described in Japanese Patent Application Publication No. 42-21,752 being useful as as a proteinaceous anticancer substance. SMANCS is synthesized by bonding two molecules of a partially half-esterified styrene-maleic acid copolymer (hereinafter abbreviated as SMA) to one molecule of NCS through an acid amide (inkage and maybe expressed as (SMA)-(NCS)-(SMACS) as described in Japanese Patent laid open, No. 60-75,432 and No. 60-75,499. SMANCS is a cancerocidal substance exhibiting an excellent anticancer activity equal to that of NCS and having a reduced toxicity and an enhanced prolonged action as compared with NCS.

If it is intended to apply SMANCS to a human body as a parenteral injection, since SMANCS itself is a peptide, it is preferable that SMANCS is lyophilized and dissolved in an aqueous solvent in use.

However, while SMANCS is stable in a dark cold place (not higher than 5° C., storage in a refrigerator), it is unstable at room, even in the lyophilized state, so that such an instability is a large obstacle when SMANCS is supplied as a drug. Therefore, a need exists it is demanded to develop a lyophilized pharmaceutical preparation of SMANCS having a high stability against heat and a good storability even at room temperature.

On the other hand, it is known that peptides having a biogenic property such as enzymes, hormones, lymphokine and the like are also unstable, not only in an aqueous solution in the liquid state but also in a lyophilized state, and are subject to a considerably loss of their biogenic properties. Therefore, the addition of a stabilizing agent is widely performed as a method of preventing the disappearance of the biogenic properties of peptides and enhancing the stability of the peptides.

For instance, D-glucose, D-galactose, D-xylose, D-glucuronic acid, trehalose, dextran, hydroxyethyl starch and the like are known as stabilizing agents in the storage, isolation, purification, lyophilization and the like of tumor necrosis factors (Japanese Patent laid open No. 59-59,625), and polysaccharides such as dextran and the like are known as a stabilizing agent for interferon (Japanese Patent laid open No. 60-59,000). As a result of various studies on stabilizing agents for interferon against heat, there are known, for example, glycerin, saccharose (Japanese Patent laid open No. 59-25,333), dextran, hydroxyethyl starch (Japanese Patent laid open No. 60-155,136), glycine, α-alanine and its salt and human serum albumin (Japanese Patent laid open No. 58-146,504), glutamic acid (Japanese Patent laid open No. 59-181,224), inorganic salts, particularly sodium chloride (Japanese Patent laid open No. 59-25,364) and the like. Further, mannitol is widely used as a stabilizing agent and an adjuvant in ordinary lyophilized preparations.

However, SMANCS is an NCS derivative obtained by bonding SMA as a polymer to NCS as a high molecular weight biogenic peptide as mentioned above, so that it is a very special cancerocidal substance possessing properties as a peptide and properties as a polymer. Therefore, the aforementioned well-known stabilizing agents for the biogenic peptide can not be applied to SMANCS as they are. In fact, the inventors have attempted the preparation of the lyophilized pharmaceutical composition of SMANCS by using glycine and serum albumin which are; well-known as stabilizing agents for peptides or mannitol, a well-known stabilizing agent and adjuvant for lyophilized preparations, but did not find an improvement in the stability thereof (see comparative Example 1-3 herein.

SUMMARY OF THE INVENTION

The inventors have made various studies with respect to the lyophilized pharmaceutical composition of SMANCS being stable against heat and found that lactose, conventionally known as an adjuvant for tablets and capsules, surprisingly develops a remarkable effect on stabilization against heat of SMANCS it the lyophilized state. Furthermore, the inventors have found that the stabilization of SMANCS is similarly attained by disaccharides other than lactose, monosaccharides, dextran and the like, and as a result the invention has been accomplished.

That is, the invention provides a lyophilized pharmaceutical composition comprising (a) SMANCS and (b) at least one saccharide selected from the group consisting of monosaccharides, disaccharides and dextran.

Here, SMANCS is a neocarzinostation derivative represented by the following formula (A):

$$(SMA)\text{-}(NCS)\text{-}(SMA) \quad (A)$$

wherein (NCS) is a divalent neocarzinostatin residue in which one hydrogen atom is removed from each of the primary amino group in alanine residue at the N-terminal of neocarzinostatin and that in lysine residue at 20th position from the N-terminal of neocarzinostatin and (SMA) is a monovalent styrene-maleic acid copolymeric residue, which may be partially half-esterified and consists of structural units for 1) styrene residue

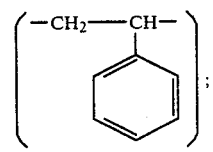

2) a residue having the following formula in which a hydroxyl group of one carboxyl group in maleic acid residue is removed and bonded to the neocarzinostatin residue

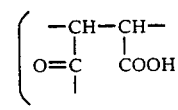

wherein the linkage of a carbon atom of a carbonyl group bonds to the neocarzinostatin residue; and 3) a) maleic acid residue

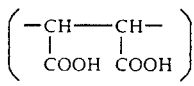

or b) half-esterified maleic acid residue

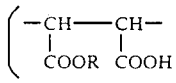

in which R is an alcohol residue wherein an hydroxyl group is removed from an alkanol having 1 to 4 carbon atoms, ethylene glycol monoalkyl ether in which the alkyl group has 1 to 2 carbon atoms or glycerine dialkyl ether wherein the alkyl group has 1 to 2 carbon atoms) and maleic acid residue

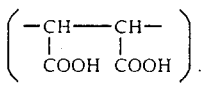

DESCRIPTION OF THE PREFERRED EMBODIMENTS

The details of SMANCS are disclosed in Japanese laid open patent application Nos. 60-75,432 and 60-75,499, a typical example of which is a compound wherein the styrene-maleic acid copolymeric residue (SMA), which may be half-esterified, is a half-butyl esterified styrene-maleic acid copolymeric residue (hereinafter abbreviated as Bu-SMANCS).

As the monosaccharide, use may be made of glucose, galactose, fructose, mannose, rhamnose and so on. As the disaccharide, use may be made of lactose, saccharose, maltose and so on. The dextran preferably has an average molecular weight of about 10,000 to 80,000, and includes for example, Dextran 10, 40 and 70 (whose average molecular weights are 10,000, 40,000, and 70,000, respectively). Among them, the disaccharides, such as lactose, saccharose, maltose and the like, are preferably used. The amount of the saccharide added is not less than 1.0 mg, preferably about 10 mg to about 50 mg per 1 mg (titer) of SMANCS.

Although the effect of the saccharide on the SMANCS and the cause of increased stability against heat in the lyophilized state is not yet clear, but is considered as follows.

In order to stably maintain the activity of SMANCS, the superstructure of the SMANCS peptide portion should be held stably. If SMANCS is lyophilized, hydration water existing around the peptide, which is required to form a hydrophobic bond relating to the holding of the superstructure of the peptide portion, is removed making the structure of the peptide unstable.

The saccharide molecule has a strong action of holding the hydration water even during the lyophilization process and can form a quasi-hydration layer by coordinating the saccharide molecule itself around the peptide molecule instead of hydration water. Upon such a mechanism, it is considered that, when the saccharide is coexistent even in the lyophilized state, the hydrophobic bond of the peptide portion in SMANCS is maintained and holds stable the superstructure thereof.

As seen from the following experimental examples, the disaccharides particularly exhibit a strong stabilizing effect among the monosaccharides, disaccharides and dextrans defined according to the invention. This is considered due to the fact that the steric configuration of the hydroxyl group in the molecular structure of the disaccharide has an optimum structure to interact through hydrogen bonding of the peptide portion of SMANCS.

The production of the composition according to the invention is carried out, for example, by dissolving SMANCS in a buffer solution, adding a saccharide thereto, adjusting the pH value, sterilizing by filtration in a known manner and then lyophilizing it. In this case, the saccharide may previously be added to the buffer solution before the dissolution of SMANCS or may simultaneously be added thereto together with SMANCS. For the buffer solution, a phosphate buffer solution, for example, a sodium monohydrogenphosphatesodium dihydrogenphosphate solution), a tris-hydrochloric acid buffer solution, a glycine-sodium hydroxide solution, an ammonium carbonate buffer solution, and the like may be used. Among the foregoing the phosphate buffer solution is preferably used. The pH of the buffer solution is 7.5–9.5, preferably about 8.5.

The composition according to the invention may properly contain the usual isotonization agent, soothing agent, adjuvant and the like, which are biogenically suitable and do not obstruct the activity of SMANCS. Useful isotonization agents include sodium chloride and the like, useful soothing agents include benzyl alcohol, xylocaine, procaine and useful like, and the adjuvants include polyvinyl pyrolidone and the like.

The pH value of the thus-obtained solution is adjusted by using hydrochloric acid, sodium hydroxide or the like to a pH=8.0±0.5, preferably to a pH=about 8.0±0.1. Thereafter, the solution is sterilized by filtration and then lyophilized to obtain the composition according to the invention. In general, the above operation is carried out below room temperature, preferably at a lower temperature which is not higher than 10° C., preferably not higher than 5° C., and under light shielding.

When the lyophilized pharmaceutical composition according to the invention is used as a preparation for injection, it is usually dissolved in an isotonization agent, such as physiological saline, glucose or the like, in use. The pH of this redissolved composition is within a range of about 7.0–9.5, preferably about 7.5–8.5.

When the pH value of the solution is less than 7.0, the acid amide bond between NCS and SMA in the molecule of SMANCS is apt to be hydrolyzed in the solution. When the pH value of the solution exceeds 9.5, the biogenic activity of SMANCS is apt to be reduced.

The lyophilized pharmaceutical composition according to the invention has excellent heat stability. Therefore, the composition according to the invention has great merit for enhancing the utility value of SMANCS as an aseptic solution, particularly an injection containing SMANCS as an effective ingredient of an carcinostatic agent.

The effect of the composition according to the invention will be concretely described with reference to the following experimental examples.

Moreover, all experiments were carried out in a dark place at an illumination of not more than 200 lux.

EXPERIMENTAL EXAMPLE 1

Temperature Stability Test of SMANCS

A lyophilized preparation was prepared by pouring Bu-SMANCS solution (containing 2.0 mg (titer) of Bu-SMANCS in 1 ml of solution, 1/80M ammonium carbonate buffer solution, pH: 8.5) into vials in an amount of 2.0 ml per vial. That is, one vial contained 4.0 mg (titer) of Bu-SMANCS.

The shelf stability at 5° C., 15° C., 25° C., 40° C. and or 50° C. was measured with respect to this preparation.

Moreover, the titer of Bu-SMANCS was determined by measuring antibacterial activity to *Micrococcus luteus* ATCC9341 according to a cylinder plate method described in The Japanese Antibiotic Drug Standard.

The measured results are represented as a residual activity (%) and shown in the following Table 1.

Moreover, the titer at the start was 100%.

TABLE 1

| Shelf temperature | Residual activity of SMANCS (%) | | | | |
|---|---|---|---|---|---|
| | after 1 week | after 2 weeks | after 4 weeks | after 8 weeks | after 12 weeks |
| 5° C. | — | — | 98.2 | 97.5 | 96.7 |
| 15° C. | — | 97.6 | 95.2 | 89.8 | 87.2 |
| 25° C. | — | 89.5 | 83.8 | 76.3 | — |
| 40° C. | 76.9 | 65.0 | 62.6 | — | — |
| 50° C. | 57.4 | 43.8 | 38.9 | — | — |

At the shelf temperature of 5° C., the residual activity was 97% after 12 weeks, so that the activity was substantially stably maintained. On the other hand, the residual activity lowered to 87% at the shelf temperature of 15° C. after 12 weeks, while at the shelf temperature of 25° C., the residual activity lowered to 76% after 8 weeks. Further, the residual activity lowered to 63% after 4 weeks at the shelf temperature of 40° C. and to 39% after 4 weeks at the shelf temperature of 50° C.

That is, the activity of Bu-SMANCS was stably maintained in a dark place i.e., (stored in a refrigerator at 5° C., but the stability was considerably lowered at a high temperature. When Bu-SMANCS was stored at room temperature for about 2 months, it was deactivated by about 25%.

EXPERIMENTAL EXAMPLE 2

Comparison Test of Various Stabilizing Agents on the Stabilization of SMANCS)

The shelf stability of the composition according to the invention was compared with those of a control and comparative products.

In this experiment, compositions obtained in the following Examples 1-7 were used as the composition according to the invention. Furthermore, the control product and comparative products were compositions obtained by the following Preparation Examples. Each of these compositions contained 4 mg (titer) of Bu-SMANCS and 5.56 mg of sodium phosphate per vial.

The shelf stabilities at 25° C. and 40° C. were measured over 12 weeks with respect to the lyophilized preparations of these compositions.

The measured results are represented as a residual activity (%) and shown in the following Table 2 (20° C.) and Table 3 (40° C.), respectively. Moreover, the titer at the start was 100%.

TABLE 2

Stabilizing effect of various additives to SMANCS (temperature 25° C.)

| Example No. | Residual activity of SMANCS (%) | | | |
|---|---|---|---|---|
| | after 2 weeks | after 4 weeks | after 8 weeks | after 12 weeks |
| 1 | 104.5 | 105.6 | 100.4 | 98.0 |
| 2 | 97.0 | 95.5 | 100.8 | 99.4 |
| 3 | 100.0 | 94.6 | 100.1 | 93.8 |
| 4 | 100.0 | 100.2 | 102.4 | 101.1 |
| 5 | 97.5 | 96.5 | 102.7 | 99.8 |
| 6 | 97.3 | 93.6 | 100.2 | 101.4 |
| 7 | 88.0 | 90.7 | 90.2 | 87.4 |
| Control | 88.7 | 84.5 | 77.3 | 72.5 |
| Comparative Example 1 | 79.1 | 70.0 | 61.2 | 48.5 |
| Comparative Example 2 | 92.3 | 84.7 | 81.0 | 68.1 |
| Comparative Example 3 | 90.2 | 86.9 | 82.4 | 78.3 |

TABLE 3

Stabilizing effect of various additives to SMANCS (temperature 40° C.)

| Example No. | Residual activity of SMANCS (%) | | | |
|---|---|---|---|---|
| | after 2 weeks | after 4 weeks | after 8 weeks | after 12 weeks |
| 1 | 98.0 | 100.8 | 93.4 | 93.3 |
| 2 | 90.8 | 89.2 | 91.7 | 87.4 |
| 4 | 96.0 | 101.7 | 98.6 | 97.7 |
| 5 | 99.3 | 93.8 | 92.8 | 95.7 |
| 6 | 99.1 | 100.7 | 91.9 | 98.0 |
| 7 | 83.3 | 78.7 | 77.5 | 71.2 |
| Control | 63.8 | 60.6 | 55.1 | 54.5 |
| Comparative Example 1 | 51.8 | 42.6 | 28.7 | 21.1 |
| Comparative Example 2 | 47.9 | 38.4 | 32.5 | 28.7 |
| Comparative Example 3 | 76.8 | 59.5 | 51.1 | 44.2 |

As seen from the above results, the residual activity of the control lowered to 73% after 12 weeks at 24° C. and 55% after 12 weeks at 40° C., while the residual activity of the composition containing monosaccharide, disaccharide or dextran was maintained at a higher level and a remarkable stabilizing effect was observed.

The stabilizing effect increased in the order of dextran→monosaccharide→disaccharide. The residual activity of the composition containing the disaccharide was approximately 100% after 12 weeks at 25° C. and was maintained at not less than 95% even after 12 weeks at 40° C.

Moreover, the shelf conditions of 40° C. and 12 weeks were chosen as a standard for evaluating the stability at room temperature over about 1 year because these conditions corresponded to conditions of 20° C. and 48 weeks or shelf condition for about 1 year when the mechanism of decomposition reaction of the substance to be tested is a simple primary reaction.

It is apparent from the above that only the monosaccharides, disaccharides and dextran defined in the invention peculiarly stabilize SMANCS among saccharides, polyvalent alcohols, neutral amino acids, human serum albumin and the like conventionally well-known as a stabilizing agent for peptides.

The preparation examples of the control and comparative products used in the above experiment will be described below. (The preparation was carried out in a dark place at a temperature of not higher than 5° C. and an illumination of not more than 200 lux.)

PREPARATION EXAMPLES OF CONTROL AND COMPARATIVE EXAMPLES 1-3

(1) Control 100 mg (titer) of Bu-SMANCS was dissolved in a buffer solution of 0.01M sodium phosphate (pH: 8.0), and adjusted to pH=8.0±0.1 with 0.2N hydrochloric acid and 0.2N sodium hydroxide, and further added with a buffer solution of 0.01M sodium phosphate up to a final liquid volume of 100 ml. The resulting solution was sterilized by filtration, poured into vials in an amount of 4 ml (4 mg (titer) of Bu-SMANCS) per vial, and then lyophilized to obtain a lyophilized pharmaceutical composition of Bu-SMANCS.

(2) Comparative Example 1

To 50 ml of Bu-SMANCS solution (containing 2.0 mg (titer) of Bu-SMANCS in 1 ml, 0.01M sodium phosphate buffer solution, pH: 8.0) was added 2.0 g of glycine, which was adjusted to pH=8.0±0.1 with 0.2N hydrochloric acid and 0.2N sodium hydroxide and then added with a buffer solution of 0.01M sodium phosphate (pH: 8.0) up to a final liquid volume of 100 ml. The resulting solution was sterilized by filtration, poured into vials in an amount of 4 ml (4 mg (titer) of Bu-SMANCS) per vial, and then lyophilized to obtain a lyophilized pharmaceutical composition of Bu-SMANCS and glycine.

(3) Comparative Example 2

The same procedure as in Comparative Example 1 was repeated except that 2.0 g of mannitol was used instead of glycine to obtain a lyophilized pharmaceutical composition of Bu-SMANCS and mannitol.

(4) Comparative Example 3

The same procedure as in Comparative Example 1 was repeated except that 0.2 g of human serum albumin was used instead of glycine to obtain a lyophilized pharmaceutical composition of Bu-SMANCS and human serum albumin.

As a clinical application of the composition according to the invention to human body, this composition is dissolved to form an injectable solution and intravenously or subcutaneously administered to patients unsuitable for oral administration such, as a cancer patient, an aged patient, an abnormal gastrointestinal patient and the like. The composition is desirably administered in an amount of 1-3 mg per dose and at 1-3 times per day. The kind of objective cancer maybe a solid tumor or a liquid tumor (leukemia). Moreover, the composition may be applied to tumors in ascites and pleural exudate.

The following examples are given as illustration of the invention and are not intended as limitations thereof. Moreover, all preparations were carried out in a dark place at a temperature of not higher than 5° C. and an illumination of not more than 200 lux.

Example 1

To 50 ml of Bu-SMANCS solution (containing 2.0 mg (titer) of Bu-SMANCS in 1 ml, 0.01M sodium phosphate buffer solution, pH: 8.0) was added 2.0 g of glucose, which was adjusted to pH=8.0±0.1 with 0.2N hydrochloric acid and 0.2N sodium hydroxide and further added with a buffer solution of 0.01M sodium phosphate up to a final liquid volume of 100 ml. The resulting solution was sterilized by filtration, poured into vials in an amount of 4 ml (4 mg (titer) of Bu-SMANCS) per vial and then lyophilized to obtain a lyophilized pharmaceutical composition of Bu-SMANCS and glucose.

Examples 2-17

The same procedure as in Example 1 was repeated except that various addition compounds as shown in the following Table 4 were used instead of glucose to obtain lyophilized pharmaceutical compositions having a composition ratio of monosaccharide, disaccharide or dextran as shown in Table 4. All of these compositions contained 4 mg (titer) of Bu-SMANCS per vial.

TABLE 4

| Example No. | Addition compound | Addition amount per vial (mg) |
|---|---|---|
| 2 | galactose | 80 |
| 3 | fructose | 80 |
| 4 | lactose | 40 |
| 5 | saccharose | 80 |
| 6 | maltose | 80 |
| 7 | dextran 40 | 80 |
| 8 | glucose | 40 |
|   | galactose | 40 |
| 9 | galactose | 40 |
|   | fructose | 40 |
| 10 | lactose | 40 |
|   | glucose | 40 |
| 11 | lactose | 40 |
|   | saccharose | 40 |
| 12 | lactose | 50 |
|   | maltose | 30 |
| 13 | lactose | 40 |
|   | dextran 40 | 40 |
| 14 | glucose | 200 |
| 15 | saccharose | 200 |
| 16 | fructose | 50 |
|   | maltose | 150 |
| 17 | saccharose | 100 |
|   | dextran 40 | 100 |

EXAMPLES 18-22

The same procedure as in Example 1 was repeated to obtain lyophilized pharmaceutical compositions having a composition ratio of Bu-SMANCS as shown in the following Table 5.

TABLE 5

| Example No. | Titer of Bu-SMANCS per vial (mg) | Saccharides addition compound | addition amount per vial (mg) |
|---|---|---|---|
| 18 | 1 | galactose | 10 |
| 19 | 1 | lactose | 50 |
| 20 | 6 | saccharose | 80 |
| 21 | 8 | glucose | 40 |
|    |   | dextran 40 | 40 |
| 22 | 10 | glucose | 200 |

What is claimed is:

1. A lyophilized pharmaceutical composition, comprising:
   a neocarzinostatin derivative and at least one saccharide selected from the group consisting of monosaccharides, disaccharides and dextran,
   wherein the neocarzinostatin derivative is represented by the following formula:

(SMA)-(NCS)-(SMA), wherein -(NCS)-is a divalent neocarzinostatin residue which has an N-terminal, which has an alanine residue therein at the N-terminal thereof having two primary amino groups and having one hydrogen atom removed from each of the two primary amino groups, and which has a lysine residue at the 20th position from the N-terminal thereof, and wherein (SMA)- is a monovalent styrene-maleic acid copolymeric residue which may be partially half-esterified and consists of structural units for:

(1) a styrene residue

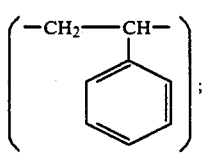

(2) a residue having the following formula in which a hydroxyl group of one carboxyl group of a maleic acid residue is removed to provide a carbonyl group and

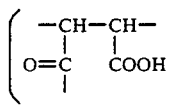

wherein the carbon of the carbonyl group is bonded to the neocarzinostatin residue); and (3) (a) a maleic acid residue

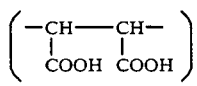

or in (3)(b) a half-esterified maleic acid residue

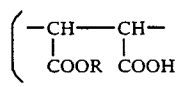

in which R is an alcohol residue wherein an hydroxyl group is removed from an alkanol having 1 to 4 carbon atoms, an ethylene glycol monoalkyl ether in which the alkyl group has 1 to 2 carbon atoms, or an glycerine dialkyl ether wherein the alkyl group has 1 to 2 carbon atoms) and a maleic acid residue

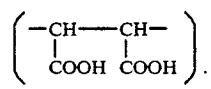

2. The composition according to claim 1, wherein the styrene-maleic acid copolymeric residue is a monovalent partially half-butyl esterified styrene-maleic acid copolymeric residue.

3. The composition according to claim 1, wherein the monosaccharide is at lest one of glucose and galactose.

4. The composition according to claim 1, wherein the disaccharide is at least one of lactose, saccharose and maltose.

5. A method of producing a stabilized lyophilized pharmaceutical composition comprised of a neocarzinostatin derivative having the formula:

(SMA)-(NCS)-(SMA), wherein -(NCS)- is a divalent neocarzinostatin residue which has an N-terminal, which has an alanine residue therein at the N-terminal thereof having two primary amino groups and having one hydrogen atom removed from each of the two primary amino groups, and which has a lysine residue at the 20th position from the N-terminal thereof, and wherein (SMA)- is a monovalent styrene-maleic acid copolymeric residue which may be partially half-esterified and consists of structural units for:

(1) a styrene residue

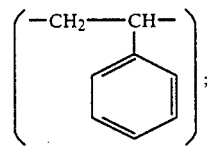

(2) a residue having the following formula in which a hydroxyl group of one carboxyl group of a maleic acid residue is removed to provide a carbonyl group and

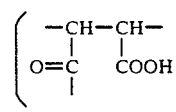

wherein the carbon of the carbonyl group is bonded to the neocarzinostatin residue); and (3)(a) a maleic acid residue

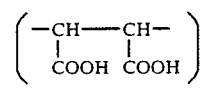

or (3)(b) a half-esterified maleic acid residue

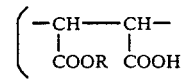

in which R is an alcohol residue wherein an hydroxyl group is removed from an alkanol having 1 to 4 carbon atoms, an ethylene glycol monoalkyl ether in which the alkyl group has 1 to 2 carbon atoms, or an glycerine dialkyl ether wherein the alkyl group has 1 to 2 carbon atoms) and a maleic acid residue

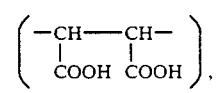

the method comprising:

a. dissolving the neocarzinostatin derivative and a stabilizing agent comprising at least one saccharide selected from the group consisting of monosaccharides, disaccharides and dextran in an aqueous buffer solution having a pH ranging from about 7.5 to about 9.5, the stabilizing agent being present in an amount by weight which is at least equal to that of the neocarzinostatin derivative to provide a solution;

b. adjusting the pH of the solution to provide a pH-adjusted solution having a pH of about 8.0±0.5;

c. sterilizing the pH-adjusted solution by filtration to provide a sterilized solution; and d. lyophilizing the sterilized solution.

6. The method according to claim 5, wherein the styrene maleic acid copolymeric residue is a monovalent partially half-butyl esterified styrene-maleic acid copolymeric residue.

7. The method according to claim 5, wherein the monosaccharide is at least one of glucose and galactose.

8. The method according to claim 5, wherein the disaccharide is at least one of lactose, saccharose and maltose.

9. The method according to claim 5, wherein said at least one saccharide is present in an amount by weight (titer) which ranges from about 10 to about 50 times that of the neocarzinostatin derivative.

10. The method according to claim 5, wherein the pH of the aqueous buffer solution of step a is adjusted in step b to a pH of about 8±0.1.

11. The process of stabilizing a lyophilized pharmaceutical composition comprised of a neocarzinostatin derivative having the formula:

(SMA)-(NCS)-(SMA), wherein -(NCS)- is a divalent neocarzinostatin residue which has an N-terminal, which has an alanine residue therein at the N-terminal thereof having two primary amino groups and having one hydrogen atom removed from each of the two primary amino groups, and which has a lysine residue at the 20th position from the N-terminal thereof, and wherein (SMA)- is a monovalent styrene-maleic acid copolymeric residue which may be partially half-esterified and consists of structural units for:

(1) a styrene residue

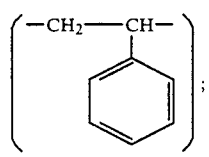

(2) a residue having the following formula in which a hydroxyl group of one carboxyl group of a maleic acid residue is removed to provide a carbonyl group and

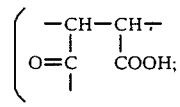

wherein the carbon of the carbonyl group is bonded to the neocarzinostatin residue); and (3)(a) a maleic acid residue

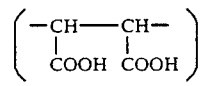

(3)(b) a half-esterified maleic acid residue

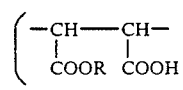

in which R is an alcohol residue wherein an hydroxyl group is removed from an alkanol having 1 to 4 carbon atoms, an ethylene glycol monoalkyl ether in which the alkyl group has 1 to 2 carbon atoms, or an glycerine dialkyl ether wherein the alkyl group has 1 to 2 carbon atoms) and a maleic acid residue

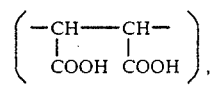

the process comprising:

a. dissolving the neocarzinostatin derivative and a stabilizing agent comprising at least one saccharide selected from the group consisting of monosaccharides, disaccharides and dextran in an aqueous buffer solution having a pH ranging from about 7.5 to about 9.5, the stabilizing agent being present in an amount by weight (titer) which is at least equal to that of the neocarzinostating derivative to provide a solution;

b. adjusting the pH of the solution to provide a pH-adjusted solution having a pH of about 8.0+0.5;

c. sterilizing the pH-adjusted solution by filtration to provide a sterilized solution; and d. lyophilizing the sterilized solution.

12. The process according to claim 11, wherein the styrene maleic acid copolymeric residue is a monovalent partially half-butyl esterified styrene-maleic acid copolymeric residue.

13. The process according to claim 11, wherein the monosaccharide is at least one of glucose and galactose.

14. The process according to claim 11, wherein the disaccharide is at least one of lactose, saccharose and maltose.

15. The process according to claim 11, wherein said at least one saccharide is present in an amount by weight (titer) which ranges from about 10 to about 50 times that of the neocarzinostatin derivative.

16. The process according to claim 11, wherein the pH of the aqueous buffer solution of step a is adjusted in step b to a pH of about 8.0+0.1.

* * * * *

UNITED STATES PATENT AND TRADEMARK OFFICE
CERTIFICATE OF CORRECTION

PATENT NO. : 5,026,772
DATED : June 25, 1991
INVENTOR(S) : Mitsugu KOBAYASHI et al.

It is certified that error appears in the above-identified patent and that said Letters Patent is hereby corrected as shown below:

Column 12

In claim 11, paragraph b, line 2, change "$8.0 + 0.5$" to --$8.0 \pm 0.5$--.

In claim 16, line 3, change "$8.0 + 0.1$" to --$8.0 \pm 0.1$--.

Signed and Sealed this

Third Day of November, 1992

*Attest:*

DOUGLAS B. COMER

*Attesting Officer*     *Acting Commissioner of Patents and Trademarks*